(12) United States Patent
Hamilton, Jr.

(10) Patent No.: US 6,437,197 B1
(45) Date of Patent: Aug. 20, 2002

(54) PROCESS FOR CATALYTIC HYDROXYLATION OF AROMATIC HYDROCARBONS

(75) Inventor: David Morris Hamilton, Jr., Sugar Land, TX (US)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 09/559,925

(22) Filed: Apr. 27, 2000

(51) Int. Cl.$^7$ ................................................ C07C 37/00
(52) U.S. Cl. ........................................ 568/802; 568/800
(58) Field of Search ........................ 568/800, 802, 568/741, 771

(56) References Cited

U.S. PATENT DOCUMENTS

| | | | |
|---|---|---|---|
| 4,683,217 A | 7/1987 | Lok et al. | 502/214 |
| 4,758,419 A | 7/1988 | Lok et al. | 423/306 |
| 5,001,280 A | 3/1991 | Gubelmann et al. | 568/716 |
| 5,055,623 A | 10/1991 | Gubelmann et al. | 568/800 |
| 5,110,995 A * | 5/1992 | Kharitonov et al. | 568/800 |
| 5,176,883 A | 1/1993 | Smith, Jr. et al. | 422/211 |
| 5,190,904 A | 3/1993 | Crossland et al. | 502/85 |
| 5,215,725 A | 6/1993 | Sy | 422/212 |
| 5,243,115 A | 9/1993 | Smith, Jr. et al. | 585/446 |
| 5,262,576 A | 11/1993 | Smith, Jr. | 585/447 |
| 5,321,181 A | 6/1994 | Smith, Jr. et al. | 585/467 |
| 5,324,702 A * | 6/1994 | Yoo et al. | 502/204 |
| 5,345,006 A | 9/1994 | Smith, Jr. et al. | 568/899 |
| 5,446,223 A | 8/1995 | Smith, Jr. | 585/313 |
| 5,476,978 A | 12/1995 | Smith, Jr. et al. | 585/323 |
| 5,672,777 A | 9/1997 | Kharitonov et al. | 568/800 |
| 5,756,861 A | 5/1998 | Panov et al. | 568/800 |
| 5,770,782 A | 6/1998 | Knifton et al. | 585/467 |
| 5,808,167 A | 9/1998 | McGhee | 568/716 |
| 5,874,646 A | 2/1999 | Ebner et al. | 568/771 |
| 5,912,391 A | 6/1999 | Barnhart et al. | 568/802 |

FOREIGN PATENT DOCUMENTS

| | | | |
|---|---|---|---|
| DE | 1184772 | * 1/1965 | |
| EP | 0043562 A1 | 1/1982 | C01B/25/36 |
| EP | 0158976 A2 | 10/1985 | C01B/33/26 |
| GB | 2116974 A | 10/1983 | |

OTHER PUBLICATIONS

"Direct Hydroxylation of Benzene to Phenol by Nitrous Oxide," by A. K. Uriarte, M. A. Rodkin, M. J. Gross, A. S. Kharitonov, and G. I. Panov, 3rd World Congress on Oxidation Catalysis, 1997 Elsevier Science B.V., pp. 857–864.
Oxidative Hydroxylation Using Dinitrogen Monoxide: A Possible Route for Organic Synthesis Over Zeolites, by G. I. Panov, A. S. Kharitonov, and V. I. Sobolev, Applied Catalysis A: General, 98 (1993) pp. 1–20.
Chemical Communications, 1998, p. 1841–1842.
"Isolated Redox Centers Within Microporous Environments 2. Vanadium–Containing Aluminophosphate Molecular Sieve Five," by C. Montes, M. E. Davis, B. Murray, and M. Narayana, *J. Phys. Chem.* 1990, 94, pp. 6431–6435.
"Isolated Redox Centers Within Microporous Environments 1. Cobalt–Containing Aluminophosphate Molecular Sieve Five," by C. Montes, M. E. Davis, B. Murray, and M. Narayana, *J. Phys. Chem.* 1990, 94, pp. 6425–6430.

* cited by examiner

*Primary Examiner*—Samuel Barts
*Assistant Examiner*—Elvis O. Price

(57) ABSTRACT

A process for increasing catalyst stability during the direct hydroxylation of liquid phase benzene or benzene derivatives with an oxidant and a solid catalyst under conditions effective to prevent coke formation on the catalyst. The process can be used to form phenol or phenol derivatives.

53 Claims, 1 Drawing Sheet

PROCESS FOR CATALYTIC HYDROXYLATION OF AROMATIC HYDROCARBONS

FIELD OF THE INVENTION

The present invention relates to a process for oxidizing aromatic compounds using an oxidant over an oxidizing catalyst under catalytic distillation conditions. More particularly, the present invention relates to hydroxylating aromatics using an oxidizing gas over a molecular sieve catalyst under catalytic distillation conditions.

BACKGROUND OF THE INVENTION

Various methods are known to produce hydroxylated aromatic compounds. The majority of such processes require either the purchase or the formation of an aromatic compound bearing a substituent besides a hydroxyl group. That preexisting substituent then is converted to a hydroxyl group. Direct hydroxylation of aromatic compounds theoretically should be more economical.

Known methods for directly hydroxylating aromatics—particularly for directly converting benzene to phenol—are gas phase processes. In such processes, benzene vapor is partially oxidized at high temperature, typically by reaction with nitrous oxide over a catalyst bed.

Gas phase direct conversion processes are less than ideal for a number of reasons. The energy required to supply the initial heat to begin the reaction is costly. In addition, the reaction of benzene and nitrous oxide is highly exothermic. Expensive, complex system designs may be required to handle the excess heat.

The expense of such reactions is further increased by coke formation from the decomposition products formed at such high temperatures. The average productivity of a catalyst for gas phase oxidation of benzene is only about 4 mmol phenol/g catalyst/hour. The coked catalyst must be regenerated at frequent intervals.

Finally, the reported selectivity of nitrous oxide to phenol in these gas phase processes is low. While selectivities of benzene to phenol of 97–98 mol % are reported, the reported selectivity of nitrous oxide to phenol is only about 85 mol %.

A more economical and efficient process is needed for directly oxidizing aromatic compounds.

SUMMARY OF THE INVENTION

The present invention provides a process comprising contacting an aromatic compound which is at least partially in a liquid phase with an oxidation catalyst and an oxidant under conditions effective to produce a hydroxylated product and an unhydroxylated product, while maintaining the aromatic compound at least partially in a liquid phase.

DETAILED DESCRIPTION OF THE INVENTION

Figure 1:
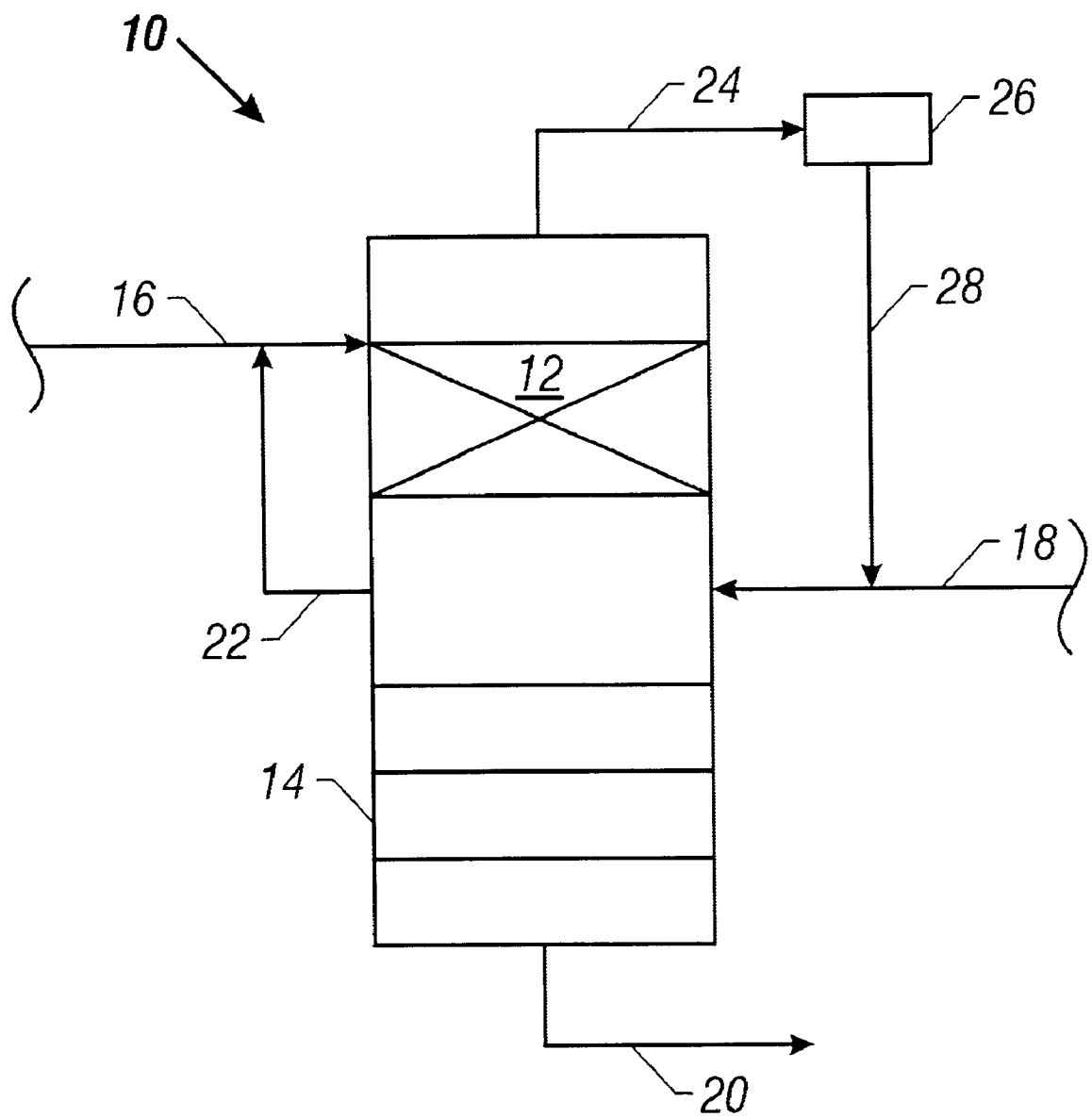
FIG. 1 is a schematic representation of one embodiment of the present invention.

The present invention relates to a process for the direct hydroxylation of aromatic compounds under catalytic distillation conditions. A portion of the aromatic compound is maintained in a liquid phase. The aromatic compound is hydroxylated by an oxidant in the presence of an oxidizing catalyst under conditions that maximize the stability of the catalyst and maximize the selectivity of the conversion of the oxidant to the hydroxylated product.

More particularly, the invention relates to a catalytic distillation process for the oxidative hydroxylation of aromatic compounds to form the respective hydroxylated derivative at a temperature and a pressure that maintains at least a portion of the aromatic compound in the liquid phase and manages the heat generated by the exothermic hydroxylation reaction. Reflux of the un-reacted aromatic compound renders the reaction substantially isothermic. Reduced operating temperatures and heat management maximize the catalyst life by reducing catalyst coking. The selectivity of the conversion of the oxidant to hydroxylated product also is increased to at least about 90 mol %, preferably to at least about 95 mol %, most preferably to at least about 99 mol %.

During catalytic distillation, the hydroxylation reaction occurs simultaneously with the distillation, the hydroxylated product being removed from the catalytic zone as it is formed. Removal of the hydroxylated product minimizes side reactions and decomposition of the hydroxylated product. The distillation zone of the reactor is maintained at a temperature and a pressure sufficient to maintain any un-reacted aromatic compound that travels from the catalytic zone to the distillation zone in the vapor phase, preferably at or above the boiling point of the aromatic compound at a given pressure. The catalytic zone is maintained at a temperature that is below the boiling point of the hydroxylated product. The un-reacted aromatic compound eventually reaches a point in the reactor where it boils, and as a result, the temperature of the reactor is controlled by the boiling point of the aromatic compound at the system pressure. The exothermic heat of the hydroxylation reaction will vaporize a portion of the un-reacted liquid aromatic compound but will not increase the temperature in the reactor. The hydroxylation reaction has an increased driving force because the hydroxylated product is removed and cannot contribute to a reverse reaction.

In a preferred process, an aromatic compound is hydroxylated using catalytic distillation to form a hydroxylated product having a higher boiling point than the aromatic compound. The hydroxylation reaction is catalyzed by an oxidation catalyst in the presence of an oxidant in a catalytic distillation reactor at conditions that also allow for fractional distillation. The hydroxylation preferably is carried out using a molecular sieve catalyst, preferably a zeolite, under conditions that maintain at least part of the aromatic compound in a liquid phase. The catalytic distillation reactor preferably provides both catalytic zones and distillation zones. The "catalytic zone" is defined as the portion of the reactor containing the catalyst where the oxidant and aromatic react to form hydroxylated product. The "distillation zone," also called the "fractionation zone," is defined as the portion of the reactor adapted to separate the hydroxylated product from the un-reacted aromatic compound. The distillation zone is a conventional fractionation column design, preferably integral with and downstream of the reaction zone.

The hydroxylated product has a higher boiling point than the oxidant and the aromatic compound, and is separated from un-reacted aromatic compound in the distillation zone of the reactor. The temperature along the reactor will vary depending upon the reactants and the products. The highest temperature will be in the bottom of the reactor, in the distillation zone, and the temperature along the column will be the boiling point of the composition at that point in the column under a given pressure. The reactor preferably is operated at a temperature and pressure effective to vaporize the aromatic compound as it approaches the distillation zone of the reactor while maintaining the hydroxlyated product in the liquid phase. The oxidant preferably remains in a gaseous state and un-reacted oxidant is withdrawn as overhead. The hydroxylated product is withdrawn from the distillation zone and any un-reacted aromatic compound may be allowed to reflux or it may be withdrawn from the distillation zone and added to the original aromatic compound feed as makeup.

In the catalytic distillation reactor, there exists both a liquid phase, or internal reflux, and a vapor phase. The liquid phase is more dense than a gas phase and allows for a more dense concentration of molecules for reaction over the catalyst. The fractionation or distillation separates hydroxylated product from un-reacted materials, providing the benefits of a combined liquid phase and vapor phase system while avoiding continual contact between the catalyst, the reactants, and the products.

A number of possible catalytic distillation reactor configurations are useful with the present invention, including but not limited to an upflow reactor, a downflow reactor, and a horizontal flow reactor. The reactor contains a reaction or catalytic zone sized to accommodate a fixed catalyst and a distillation zone designed to separate the hydroxylated product from un-reacted materials. The distillation zone may be integral with the reaction or catalytic zones or may be a separate column. Examples of suitable catalytic distillation reactors are found in U.S. Pat. Nos. 5,476,978; 5,262,576; 5,176,883; 5,243,115; 5,321,181; 5,345,006; 5,215,725; 5,770,782; 5,446,223; and 5,190,904, incorporated by reference herein.

Overall catalytic distillation column design and process conditions will vary depending upon the reactants used and can be determined by one of ordinary skill in the art. Suitable process conditions can be found in U.S. Pat. Nos. 5,476,978; 5,262,576; 5,176,883; 5,243,115; 5,321,181; 5,345,006; 5,215,725; 5,770,782; 5,446,223 and 5,190,904. Although these patents discuss alkylation of aromatics, the temperature and pressure can be adjusted by one of ordinary skill in the art based on the properties of the reactants including the aromatic compound and the oxidant, to effectively hydroxylate the aromatic and to separate the hydroxylated product from the reactants based on their respective boiling points at a given pressure.

In a preferred embodiment, the catalytic zone and the distillation zone are in a single column. The catalytic zone contains an amount of catalyst and the distillation zone contains a number of conventional separation trays. The aromatic compound preferably is delivered to the column above the catalyst and the oxidant is fed to the column below the catalyst. Any un-reacted aromatic compound is either withdrawn from the column once it leaves the catalytic zone, preferably as a vapor, and supplied as makeup or allowed to reflux. The overhead is withdrawn from the column above the catalytic zone and typically will contain a mixture consisting mostly of oxidant and a small amount of aromatic compound. The oxidant preferably is separated from the aromatic compound by conventional means and recycled as makeup.

Suitable oxidation catalysts are those that will catalyze the hydroxylation of an aromatic compound in the presence of an oxidant. Suitable oxidation catalysts include but are not necessarily limited to molecular sieves, including zeolites and non-zeolite materials.

Preferred zeolite catalysts are modified zeolites, preferably of the MFI structural type, most preferably ZSM-5, ZSM-11, and beta zeolite. Such zeolites are commercially available from Zeolyst International, Inc. and ExxonMobil Corporation. The zeolite catalyst preferably comprises at least one metal selected from the group consisting of ruthenium, rhodium, and iridium, preferably from about 0.01 wt. % to about 0.5 wt. %, most preferably from about 0.1 wt. % to about 1.5 wt. %. The metal can be incorporated into the catalyst by any means known to those skilled in the art for incorporating metals into zeolites such as, by ion exchange or during synthesis of the catalyst. In a preferred embodiment, the zeolite catalyst contains an amount of iron, preferably up to about 0.5 wt. %, more preferably from about 0.01 wt. % to about 1.5 wt. %. Additional examples of suitable zeolite catalysts can be found in U.S. Pat. Nos. 5,672,777; 5,808,167; 5,110,995; 5,874,646; which are incorporated by reference herein.

Non-zeolitic molecular sieves also may be used to catalyze the hydroxylation of aromatics. Suitable non-zeolitic molecular sieves include but are not necessarily limited to microporous aluminum phosphates (AlPO's) or silica aluminum phosphates (SAPO's) containing metals that are capable of being oxidized and reduced, such as, Co, V, Mn, Mg, and Fe. These catalysts consist of AlPO's or SAPO's with a fraction of the Al or phosphate ions being replaced during synthesis by a transition metal ion, from about 0.001 wt. % to about 0.6 wt. %, preferably 0.01 wt. % to about 0.4 wt. %. Synthesis of Mn-containing AlPO has been shown to hydroxylate dodecene to dodecanol using air as the oxidant as described in *Chem. Commun.* 1998, pp. 1841–1842, which is incorporated by reference herein. Alternatively, the transition metal may be incorporated into the framework of the catalyst after synthesis of the catalyst using known means including but not necessarily limited to ion exchange, impregnation, co-mulling, and physical admixing. Additional examples of suitable non-zeolitic molecular sieves and their methods of preparation can be found in U.S. Pat. Nos. 4,683,217 and 4,758,419; European patent nos. EP 0 043 562, EP 0 158 976; *J. Phys. Chem.* 1990, vol. 94, pp. 6425–6464, and pp. 6431–6435.

Another non-zeolite catalyst suitable for use in the present invention includes vanadium-peroxide complexes formed by using hydroquinones to produce peroxide species, which are transferred to the vanadium complexes. The vanadium-peroxide complexes can be used to hydroxylate aromatic compounds. A description of this method can be found in U.S. Pat. No. 5,912,391, incorporated by reference herein.

Any suitable oxidant may be used. Examples of oxidizing gases include but are not necessarily limited to, nitrous oxide, oxygen, and air. A preferred oxidant for use with zeolite catalysts is nitrous oxide. Regardless of the oxidant used, the molar ratio of oxidant to aromatic compound is from about 1:100, preferably about 1:10, most preferably about 1:3, more preferably bout 1:1. In practice, the oxidant to aromatic compound ratio is the stoichiometric ratio that will yield the desired product.

Where the product desired is phenol, the preferred aromatic compound is benzene. Other hydroxylated aromatics may be produced using the current method, benzene derivatives suitable for such hydroxylation include but are not necessarily limited to phenol, fluorobenzene, chlorobenzene, toluene, ethylbenzene, and similar compounds having an aromatic ring with a substitutable hydrogen atom on the ring.

The process will be described with reference to benzene, but the process is not limited to benzene and may be used with any aromatic compound. In a preferred embodiment, catalytic distillation is carried out in a distillation column reactor at a temperature and pressure effective to hydroxylate the benzene while fractionating or removing the hydroxylated product, phenol, from the oxidant and un-reacted benzene. The temperature in the distillation zone of the reactor is higher than the temperature in the catalytic zone of the reactor, creating a temperature gradient within the reactor of from about 50° C. to about 400° C., preferably from about 80° C. to about 300° C. such that the lower boiling components are vaporized and migrate toward the upper portion of the reactor while the higher boiling components migrate toward the lower portion of the reactor. The temperature in the lower portion of the column preferably is higher than the boiling point of benzene but lower than the boiling point of the phenol product to achieve an effective separation of the phenol product from the benzene. The pressure in the column is from about 0.2 atm to about 50 atm, preferably from about 0.5 atm to about 30 atm.

The benzene may be added at any point in the reactor, for example it may be added to the fixed bed catalyst or to the reflux as makeup. At least a portion of the benzene, preferably from about 10% to about 100%, is fed to the reactor in a liquid state. The oxidant preferably is a gas, and is fed to the reactor at a point below the catalyst bed allowing the oxidant to flow upward into the catalyst bed where the oxidant contacts and reacts with the benzene. Once in the reactor, the benzene contacts the catalyst and the oxidant, and the benzene is hydroxylated to form phenol. Phenol has a higher boiling point (182° C.) than benzene (80° C.), which allows for easy separation by fractional distillation.

The overhead taken from the distillation column preferably is partially condensed to separate the un-reacted benzene from the un-reacted oxidant. The partially condensed overheads are passed to an accumulator where benzene is collected and the gaseous oxidant is taken off. The benzene and the oxidant can be fed back to the distillation column. Preferably, heat generated by the hydroxylation reaction is removed from the reactor by the reflux of the un-reacted organic compounds, allowing for isothermal operation of the system. Regulating the heat in the reactor also extends the catalyst life.

The process can be used to hydroxylate other organics such as branched olefins to produce branched alcohols which are useful as surfactants. Linear alcohols may be produced by hydroxylating linear olefins in a similar manner.

The zeolite catalyst is believed to catalyze the following reaction, when the aromatic compound is benzene and the oxidant is nitrous oxide:

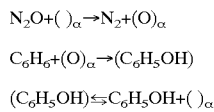

where the formation of the alpha oxygen $(O)_\alpha$ is critical. The formation of $(O)_\alpha$ is dependent upon the iron content in the zeolite. The $(O)_\alpha$ will form at low temperatures provided there is sufficient iron present in the zeolite. Once the $(O)_\alpha$ has formed, desorption of $(O)_\alpha$ as $O_2$ does not occur at temperatures below 300° C. to 330° C., which means that $(O)_\alpha$ can be isolated on the catalyst at moderate temperatures. It is believed that the $(O)_\alpha$ oxygen from the $N_2O$ will remain on the catalyst until it is reacted with the benzene, thus increasing the amount of $(O)_\alpha$ used to form phenol. It has been shown that benzene will react with $(O)_\alpha$ at ambient temperatures (e.g. 50° C.) to form phenol at high yields.

However, the phenol formed is bound to the catalyst. It is believed that oxidative hydroxylation under catalytic distillation conditions will prevent the hydroxylated product from binding to the catalyst.

It is believed that the non-zeolite molecular sieves will catalyze the oxidative hydroxylation of aromatic compounds in the presence of an oxidant under catalytic distillation conditions. Non-zeolite molecular sieves have been shown to catalyze oxidative hydroxylation reactions of gaseous aromatic compounds similar to those reported for zeolite. In addition, non-zeolite molecular sieves have similar structural and re-dox properties to zeolites.

FIG. 1 illustrates one embodiment of the present invention for the production of phenol. A distillation column reactor 10 has a middle portion that contains a catalyst 12 and a lower portion of the reactor contains a conventional distillation column 14 with a sufficient number of trays to allow for the separation of the phenol product from any un-reacted benzene. The benzene is fed to the reactor through line 16 above the catalyst 12 and the oxidant gas is fed to reactor 10 through line 18 below the catalyst 12. The reaction is exothermic and is initiated by contacting the oxidant and the benzene in the presence of the catalyst. Phenol is the principal reaction product. Phenol has a higher boiling point than the benzene and the oxidant and is recovered from the column via line 20. The temperature in the reactor below the catalyst bed is higher than the boiling point of benzene and lower than the boiling point of phenol to facilitate the separation of the benzene from the phenol. Un-reacted benzene can be withdrawn from the reactor 10 via line 22 and added as makeup to the benzene fed through line 16 into the reactor 10. Alternatively, the un-reacted benzene is allowed to reflux. The oxidant is withdrawn as overhead through line 24 and passed to a condenser 26 to separate any entrained benzene from the oxidant. The recovered oxidant may then be added as makeup via line 28 to the fresh oxidant feed.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

I claim:

1. A process comprising:
   contacting an aromatic compound comprising an aromatic ring and a substitutable hydrogen atom on said aromatic ring with a non-zeolitic oxidation catalyst and an oxidant under conditions effective to hydroxylate said aromatic compound to produce a hydroxylated product and an unreacted aromatic compound, while maintaining at least a portion of said aromatic compound in a liquid phase, wherein said non-zeolitic oxidation catalyst is selected from the group consisting non-zeolitic molecular sieves and vanadium-peroxide complexes; and
   separating said hydroxylated product from said unreacted aromatic compound.

2. The process of claim 1 wherein said separating comprises fractional distillation.

3. The process of claim 1 wherein said oxidant is selected from the group consisting of nitrous oxide, oxygen, air, and mixtures thereof.

4. The process of claim 2 wherein said oxidant is selected from the group consisting of nitrous oxide, oxygen, air, and mixtures thereof.

5. The process of claim 1 wherein said oxidant is nitrous oxide.

6. The process of claim 2 wherein said oxidant is nitrous oxide.

7. The process of claim 1 wherein said conditions comprise a temperature of from about 50° C. to about 400° C.

8. The process of claim 2 wherein said conditions comprise a temperature of from about 50° C. to about 400° C.

9. The process of claim 3 wherein said conditions comprise a temperature of from about 50° C. to about 400° C.

10. A process comprising:
    contacting an aromatic compound with an oxidation catalyst and an oxidant under conditions effective to hydroxylate said aromatic compound to produce a hydroxylated product and an unreacted aromatic compound, while maintaining at least a portion of said aromatic compound in a liquid phase; and
    separating said hydroxylated product from said unreacted aromatic compound;
    wherein said catalyst is selected from the group consisting of microporous aluminum phosphate or silica aluminum phosphate containing a metal selected from the group consisting of Co, V, Mn, Mg, and Fe.

11. A process comprising:
    contacting an aromatic compound with an oxidation catalyst and an oxidant under conditions effective to hydroxylate said aromatic compound to produce a hydroxylated product and an unreacted aromatic compound, while maintaining at least a portion of said aromatic compound in a liquid phase; and
    separating said hydroxylated product from said unreacted aromatic compound by fractional distillation;
    wherein said catalyst is selected from the group consisting of microporous aluminum phosphate or silica aluminum phosphate containing a metal selected from the group consisting of Co, V, Mn, Mg, and Fe.

12. A process comprising:
    contacting an aromatic compound with an oxidation catalyst and an oxidant selected from the group consisting of nitrous oxide, oxygen, air, and mixtures thereof under conditions effective to hydroxylate said aromatic compound to produce a hydroxylated product and an unreacted aromatic compound, while maintaining at least a portion of said aromatic compound in a liquid phase; and
    separating said hydroxylated product from said unreacted aromatic compound;
    wherein said catalyst is selected from the group consisting of microporous aluminum phosphate or silica aluminum phosphate containing a metal selected from the group consisting of Co, V, Mn, Mg, and Fe.

13. The process of claim 1 wherein said conditions comprise a pressure of from about 0.2 atm to about 50 atm.

14. The process of claim 2 wherein said conditions comprise a pressure of from about 0.2 atm to about 50 atm.

15. The process of claim 3 wherein said conditions comprise a pressure of from about 0.2 atm to about 50 atm.

16. The process of claim 5 wherein said conditions comprise a pressure of from about 0.2 atm to about 50 atm.

17. The process of claim 1 wherein said separating is carried out in a separation zone under conditions effective to vaporize said unreacted aromatic compound and maintain said hydroxylated product in a liquid phase.

18. The process of claim 17 wherein said separating conditions comprise maintaining said separation zone at a temperature effective to maintain said hydroxylated product in a liquid phase and said unreacted aromatic compound in a vapor phase.

19. The process of claim 1 further comprising withdrawing said unreacted aromatic compound as overhead.

20. A process comprising
    contacting an aromatic compound comprising an aromatic ring and a substitutable hydrogen atom on said aromatic ring with an oxidant in a distillation column reactor at a temperature of from about 50° C. to about 400° C. to form a hydroxylated product and an unreacted aromatic compound, at least a portion of said aromatic compound being in a liquid phase, said distillation column reactor comprising a non-zeolitic oxidizing catalyst effective to hydroxylate said aromatic compound, wherein said non-zeolitic oxidation catalyst is selected from the group consisting of non-zeolitic molecular sieves and vanadium-peroxide complexes; and
    separating said hydroxylated product from said unreacted aromatic compound.

21. The process of claim 20 wherein said separating is carried out in a distillation zone under conditions effective to vaporize said unreacted aromatic compound and maintain said hydroxylated product in a liquid phase.

22. The process of claim 21 wherein said distillation zone is maintained at a temperature effective to maintain said hydroxylated product in a liquid phase and said unreacted aromatic compound in a vapor phase.

23. The process of claim 21 further comprising withdrawing said vaporized unreacted aromatic compound and oxidant as overhead.

24. The process of claim 20 wherein said oxidant is nitrous oxide.

25. The process of claim 24 wherein selectivity for conversion of nitrous oxide to phenol is at least about 90 mol %.

26. A process comprising
    contacting an aromatic compound with an oxidant in a distillation column reactor at a temperature of from about 50° C. to about 400° C. to form a hydroxylated product and an unreacted aromatic compound, at least a portion of said aromatic compound being in a liquid phase, said distillation column reactor comprising an oxidizing catalyst effective to hydroxylate said aromatic compound; and
    separating said hydroxylated product from said unreacted aromatic compound;
    wherein said catalyst is selected from the group consisting of microporous aluminum phosphate or silica aluminum phosphate containing a metal selected from the group consisting of Co, V, Mn, Mg, and Fe.

27. The process of claim 1 wherein selectivity for conversion of said oxidant to hydroxylated product is at least 90 mol %.

28. The process of claim 1 wherein selectivity for conversion of said oxidant to hydroxylated product is at least 95 mol %.

29. The process of claim 1 wherein said hydroxylated product comprises phenol and said unreacted aromatic compound comprises benzene.

30. The process of claim 10 wherein said hydroxylated product comprises phenol and said unreacted aromatic compound comprises benzene.

31. The process of claim 20 wherein said hydroxylated product comprises phenol and said unreacted aromatic compound comprises benzene.

32. The process of claim 26 wherein said hydroxylated product comprises phenol and said unreacted aromatic compound comprises benzene.

33. The process of claim 2 wherein said separating is carried out in a distillation zone under conditions effective to vaporize said unreacted aromatic compound and maintain said hydroxylated product in a liquid phase.

34. The process of claim 33 wherein said distillation zone is maintained at a temperature effective to maintain said hydroxylated product in a liquid phase and said unreacted aromatic compound in a vapor phase.

35. The process of claim 34 further comprising withdrawing said vaporized unreacted aromatic compound and oxidant as overhead.

36. The process of claim 35 wherein said hydroxylated product comprises phenol and said unreacted aromatic compound comprises benzene.

37. The process of claim 10 wherein said separating is carried out in a distillation zone under conditions effective to vaporize said unreacted aromatic compound and maintain said hydroxylated product liquid phase.

38. The process of claim 37 wherein said distillation zone is maintained at a temperature effective to maintain said hydroxylated product in a liquid phase and said unreacted aromatic compound in a vapor phase.

39. The process of claim 38 further comprising withdrawing said vaporized unreacted aromatic compound and oxidant as overhead.

40. The process of claim 39 wherein said hydroxylated product comprises phenol and said un-reacted aromatic compound comprises benzene.

41. The method of claim 10 wherein said aromatic compound comprises an aromatic ring comprising a substitutable hydrogen atom on said ring.

42. The method of claim 11 wherein said aromatic compound comprises an aromatic ring comprising a substitutable hydrogen atom on said ring.

43. The method of claim 12 wherein said aromatic compound comprises an aromatic ring comprising a substitutable hydrogen atom on said ring.

44. The method of claim 1 wherein said aromatic compound is selected from the group consisting of benzene, phenol, fluorobenzene, chlorobenzene, toluene and ethylbenzene.

45. The method of claim 10 wherein said aromatic compound is selected from the group consisting of benzene, phenol, fluorobenzene, chlorobenzene, toluene and ethylbenzene.

46. The method of claim 11 wherein said aromatic compound is selected from the group consisting of benzene, phenol, fluorobenzene, chlorobenzene, toluene and ethylbenzene.

47. The method of claim 12 wherein said aromatic compound is selected from the group consisting of benzene, phenol, fluorobenzene, chlorobenzene, toluene and ethylbenzene.

48. The method of claim 20 wherein aromatic compound is selected from the group consisting of benzene, phenol, fluorobenzene, chlorobenzene, toluene and ethylbenzene.

49. The method of claim 26 wherein said aromatic compound is selected from the group consisting of benzene, phenol, fluorobenzene, chlorobenzene, toluene and ethylbenzene.

50. The method of claim 10 wherein said non-zeolitic oxidation catalyst is selected from the group consisting of non-zeolitic molecular sieves and vanadium-peroxide complexes.

51. The method of claim 11 wherein said non-zeolitic oxidation catalyst is selected from the group consisting of non-zeolitic molecular sieves and vanadium-peroxide complexes.

52. The method of claim 12 wherein said non-zeolitic oxidation catalyst is selected from the group consisting of non-zeolitic molecular sieves and vanadium-peroxide complexes.

53. The method of claim 26 wherein said non-zeolitic oxidation catalyst is selected from the group consisting of non-zeolitic molecular sieves and vanadium-peroxide complexes.

* * * * *